United States Patent
Hine (10) Patent No.: US 9,802,681 B1
(45) Date of Patent: *Oct. 31, 2017

(54) AUTONOMOUS WAVE-POWERED VESSELS AND FLEETS FOR MANAGING FISH STOCK

(71) Applicant: Liquid Robotics Inc., Sunnyvale, CA (US)

(72) Inventor: Roger G. Hine, Menlo Park, CA (US)

(73) Assignee: LIQUID ROBOTICS, INC., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/197,091

(22) Filed: Mar. 4, 2014

Related U.S. Application Data (62) Division of application No. 13/424,239, filed on Mar. 19, 2012, now Pat. No. 8,825,241.

(Continued)

(51) Int. Cl.
*B63B 35/00* (2006.01)
*B63B 21/66* (2006.01)
(Continued)

(52) U.S. Cl.
CPC .............. *B63B 35/00* (2013.01); *A01K 61/00* (2013.01); *A01K 61/80* (2017.01); *A01K 61/90* (2017.01);
(Continued)

(58) Field of Classification Search
None
See application file for complete search history.

(56) References Cited

U.S. PATENT DOCUMENTS

| 986,627 A | 3/1911 | Fisher |
| 1,067,113 A | 7/1913 | Heyen |

(Continued)

FOREIGN PATENT DOCUMENTS

| BE | 570555 | 9/1958 |
| CN | 1280936 | 1/2001 |

(Continued)

OTHER PUBLICATIONS

Green, Dale. "Underwater acoustic communication and modem-based navigation aids." International Conference on Embedded and Ubiquitous Computing. Springer Berlin Heidelberg, 2007.*

(Continued)

*Primary Examiner* — Genna Mott
(74) *Attorney, Agent, or Firm* — Gates & Cooper LLP (57) ABSTRACT

This disclosure provides wave-powered vessels equipped for fish stock management. The vessels have observational sensors for monitoring fish, a positional sensor to determine the geographical location of the vessel, and a transmitter for sending data to a central control unit. The observational sensors may be deployed on a tow body pulled behind the vessel, or the tow body may relay information from sensors located on a separate unit on the bottom or at a defined depth. The control unit communicates with each of the monitor vessels to direct navigation and obtain data from the sensors. Substance distribution vessels in the fleet are equipped to distribute fish food in target area for the purpose of fish farming.

19 Claims, 6 Drawing Sheets

Related U.S. Application Data (60) Provisional application No. 61/502,279, filed on Jun. 28, 2011, provisional application No. 61/453,862, filed on Mar. 17, 2011.

(51) Int. Cl.
  *B63H 19/02* (2006.01)
  *A01K 61/80* (2017.01)
  *A01K 61/90* (2017.01)
  *A01K 61/00* (2017.01)

(52) U.S. Cl.
  CPC ............ *B63B 21/66* (2013.01); *B63H 19/02* (2013.01); *B63B 2211/02* (2013.01); *Y02P 60/64* (2015.11); *Y02T 70/59* (2013.01)

(56) References Cited

U.S. PATENT DOCUMENTS

| | | |
|---|---|---|
| 1,315,267 A | 9/1919 | White |
| 2,170,914 A | 8/1939 | Rummier |
| 2,520,804 A | 8/1950 | Hollar |
| 2,668,512 A | 2/1954 | Klas |
| 3,132,322 A | 5/1964 | Maes |
| 3,297,814 A | 1/1967 | McClean et al. |
| 3,312,186 A | 4/1967 | Litshiem |
| 3,352,274 A | 11/1967 | Clakins |
| 3,443,020 A | 5/1969 | Loshigian |
| 3,453,981 A | 7/1969 | Gause |
| 3,508,516 A | 4/1970 | Root |
| 3,613,627 A | 10/1971 | Kennedy |
| 3,760,441 A | 9/1973 | Handelman |
| 3,828,380 A | 8/1974 | Lebovits et al. |
| 3,845,733 A | 11/1974 | Jackman |
| 3,859,949 A | 1/1975 | Toussaint et al. |
| 3,860,900 A | 1/1975 | Scudder |
| 3,872,819 A | 3/1975 | Pickens |
| 3,889,045 A | 6/1975 | Logsdon |
| 3,928,967 A | 12/1975 | Salter |
| 3,962,982 A | 6/1976 | Marchay et al. |
| 3,978,813 A | 9/1976 | Pickens et al. |
| 4,134,023 A | 1/1979 | Salter |
| 4,224,707 A | 9/1980 | Mariani |
| 4,224,951 A | 9/1980 | Hasson |
| 4,225,951 A * | 9/1980 | Menin ..................... G01S 15/96 367/105 |
| 4,332,571 A | 6/1982 | Jakobsen |
| 4,371,347 A | 2/1983 | Jakobsen |
| 4,383,725 A | 5/1983 | Bogese et al. |
| 4,389,843 A | 6/1983 | Lamberti |
| 4,462,211 A | 7/1984 | Linderfelt |
| 4,598,547 A | 7/1986 | Danihel |
| 4,610,212 A | 9/1986 | Petrovich |
| 4,638,588 A | 1/1987 | Abadie |
| 4,673,363 A | 6/1987 | Hudson et al. |
| 4,684,350 A | 8/1987 | DeLima |
| 4,684,359 A | 8/1987 | Herrington |
| 4,726,314 A | 2/1988 | Ayers |
| 4,763,126 A | 8/1988 | Jawetz |
| 4,842,560 A | 6/1989 | Lee |
| 4,896,620 A | 1/1990 | Jones |
| 4,968,273 A | 11/1990 | Momot |
| 4,981,453 A | 1/1991 | Krishan et al. |
| 5,050,519 A | 9/1991 | Senften |
| 5,084,630 A | 1/1992 | Azimi |
| 5,577,942 A | 11/1996 | Juselis |
| 5,675,116 A | 10/1997 | Hillenbrand |
| 5,678,504 A | 10/1997 | Toplosky et al. |
| 5,690,014 A | 11/1997 | Larkin |
| 5,902,163 A | 5/1999 | Barruzzi et al. |
| 6,097,424 A * | 8/2000 | Zernov ..................... H04N 7/18 348/373 |
| 6,099,368 A | 8/2000 | Gorshkov |
| 6,194,815 B1 | 2/2001 | Carroll |
| 6,260,501 B1 | 7/2001 | Agnew |
| 6,285,807 B1 | 9/2001 | Walt et al. |
| 6,408,792 B1 | 6/2002 | Markels |
| 6,561,856 B1 | 5/2003 | Gorshkov |
| 6,814,633 B1 | 11/2004 | Huang |
| 6,883,736 B1 * | 4/2005 | Blatt ..................... A01C 15/04 222/626 |
| 6,908,229 B2 | 6/2005 | Landrieve et al. |
| 6,980,228 B1 | 12/2005 | Harper |
| 7,350,475 B2 | 4/2008 | Borgwarth et al. |
| 7,371,136 B2 | 5/2008 | Hine et al. |
| D578,463 S | 10/2008 | Tureaud et al. |
| 7,641,524 B2 | 1/2010 | Hine et al. |
| 7,955,148 B2 | 6/2011 | Corradini |
| 8,043,133 B2 | 10/2011 | Hine et al. |
| 8,205,570 B1 | 6/2012 | Tureaud et al. |
| 8,944,866 B2 | 2/2015 | Hine |
| 2002/0178990 A1 | 12/2002 | McBride et al. |
| 2003/0009286 A1 | 1/2003 | Shibusawa et al. |
| 2003/0174206 A1 | 9/2003 | Moroz |
| 2003/0220027 A1 | 11/2003 | Gorshkov |
| 2004/0102107 A1 | 5/2004 | Gorshkov |
| 2004/0217597 A1 | 11/2004 | Carroll et al. |
| 2005/0268834 A1 * | 12/2005 | Koda ..................... A63H 23/04 114/144 RE |
| 2006/0213167 A1 | 9/2006 | Koselka |
| 2007/0051292 A1 | 3/2007 | Kilbourn et al. |
| 2007/0173141 A1 | 7/2007 | Hine et al. |
| 2008/0188150 A1 | 8/2008 | Hine et al. |
| 2008/0225643 A1 * | 9/2008 | Vosburgh ............... H04B 13/02 367/131 |
| 2008/0294309 A1 | 11/2008 | Kaprielian |
| 2008/0299843 A1 | 12/2008 | Hine et al. |
| 2009/0107388 A1 | 4/2009 | Crowell |
| 2009/0193715 A1 | 8/2009 | Wilcox |
| 2009/0293788 A1 * | 12/2009 | McNabb ................. B63B 35/00 114/27 |
| 2009/0311925 A1 | 12/2009 | Hine et al. |
| 2010/0268390 A1 | 10/2010 | Anderson |
| 2011/0067641 A1 * | 3/2011 | Kithil ..................... A01K 61/00 119/215 |
| 2012/0006277 A1 | 1/2012 | Troy et al. |
| 2012/0029696 A1 | 2/2012 | Ota |
| 2012/0029718 A1 | 2/2012 | Davis |
| 2012/0069702 A1 | 3/2012 | Muyzert et al. |
| 2012/0094556 A1 | 4/2012 | Hine et al. |
| 2012/0285160 A1 | 11/2012 | Hine et al. |
| 2012/0295499 A1 | 11/2012 | Hine |
| 2014/0038477 A1 | 2/2014 | Hine et al. |
| 2014/0116311 A1 | 5/2014 | Holemans |
| 2014/0263851 A1 | 9/2014 | Hine et al. |

FOREIGN PATENT DOCUMENTS

| | | |
|---|---|---|
| CN | 1132757 | 12/2003 |
| CN | 2689229 | 3/2005 |
| CN | 1715136 | 1/2006 |
| DE | 10141805 | 5/2002 |
| DE | 10300599 | 7/2004 |
| DE | 102007053037 | 5/2009 |
| DE | 202008013757 | 4/2010 |
| EP | 1369013 | 12/2003 |
| FR | 1159028 | 6/1958 |
| FR | 2669886 | 6/1992 |
| GB | 2461792 | 1/2010 |
| JP | S55-051697 | 4/1970 |
| JP | S55-152698 | 11/1980 |
| JP | S61-057488 | 3/1986 |
| JP | S63-149289 | 6/1988 |
| TW | 221588 | 3/1994 |
| TW | 547434 | 7/2003 |
| WO | 87/04401 | 7/1987 |
| WO | 94/10029 | 5/1994 |
| WO | 98/39205 | 9/1998 |
| WO | 98/46065 | 10/1998 |
| WO | 01/42992 | 6/2001 |
| WO | 2007/087197 | 8/2007 |
| WO | 2007087197 | 8/2007 |

(56) References Cited

FOREIGN PATENT DOCUMENTS

| WO | 2008/109002 | 9/2008 |
|---|---|---|
| WO | 2008109002 | 9/2008 |
| WO | 2013/077931 | 5/2013 |

OTHER PUBLICATIONS

LeBlanc, Lester R. "Coherent Path Beamforming Front End for High Performance Acoustic Modems" Florida Atlantic Univ. Boca Raton Dept of Ocean Engineering, 1999 (10 pages).*
"Persistent Ocean Surveillance Station-Keeping," Defense Advanced Research Projects Agency (DARPA) Strategic Technology Office (STO), 1 page (2005).
"Persistent Ocean Surveillance, Station-Keeping Buoys: Program Overview," Defense Advanced Research Projects Agency (DARPA) Strategic Technology Office (STO), 19 pages (2004).
Ageev, "Application of Solar and Wave Energies for Long-Range Autonomous Underwater Vehicles," Advanced Robotics 16(1): 43-55 (2002).
Anderson et al., "Towards a Comprehensive Regional Acoustic Study for Marine Mammal Distribution and Activity Regulation," A Liquid Robotics White Paper, 12 pages (2012).
Clement et al., "Wave Energy in Europe: Current Status and Perspectives," Renewable and Sustainable Energy Reviews 6(5): 405-431 (2002).
Jones et al., "Engineering a Large Sustainable World Fishery," Environmental Conservation 24(2): 99-104 (1997).
Lenton et al., "The Radiative Forcing Potential of Different Climate Geoengineering Options," Atmospheric Chemistry and Physics Discussions 9: 2559-2606 (2009).
Liquid Robotics brochure, retrieved from http://liquid.com/resources/press-hik.html, 48 pages (2011).
Martin et al., "Iron Deficiency Limits Phytoplankton Growth in the North-East Pacific Subarctic," Nature 331 (6154): 341-343 (1988).
Martin, "Glacial-Integral CO2 Change. The Iron Hypothesis," Paleoceanography 5(1): 1-13 (1990).
Masters, "Liquid Robotics Ocean Robots Embark on World Record Journey Across Pacific Ocean to Foster New Scientific Discoveries," Liquid Robotics press release, 2 pages (2011).
Olson, "Communications Architecture of the Liquid Robotics Wave Glider," 5 pages.
Phelps, "Wave-Powered Motor Propels Model Boat," Popular Mechanics 91(8): 182-183 (1949).
Rainville, "Wirewalker: An Autonomous Wave-Powered Vertical Profiler," Journal of Atmospheric and Oceanic Technology 18(6): 1048-1051 (2001).
Shaw, "The Autonaut," The American Monthly Review of Reviews 19, 2 pages (1899).
Solomon et al., "Irreversible Climate Change due to Carbon Dioxide Emission," Proceedings of the National Academy of Sciences 106(6): 1704-1709 (2009).
Sparks, "Persistent UnManned Autonomous Buoy (PUMA)," Office Naval Research (ONR) and Marine Technology Society (MTS) Buoy Workshop, SeaLandAire Technologies, Inc., 26 pages (2006).
Wilcox et al., "An Autonomous Mobile Platform for Underway Surface Carbon Measurements in Open-Ocean and Coastal Water," OCEANS 2009, Marine Technology Society (MTS) and Institute of Electrical and Electronics Engineers (IEEE), pp. 1-8, (2009).
International Search Report and Written Opinion for PCT Application No. PCT/US2008/002743 dated Sep. 2, 2008.
Office Action for Japanese Patent Application No. 2008-551327 dated Oct. 18, 2011.
International Search Report and Written Opinion for PCT Application No. PCT/US2012/029703 dated Oct. 17, 2012.
International Search Report and Written Opinion for PCT Application No. PCT/US2012/044729 dated Oct. 17, 2012.
International Search Report and Written Opinion for PCT Application No. PCT/US2012/029718 dated Dec. 21, 2012.
Extended European Search Report and Opinion for EPO Application No. 08726305 dated Jan. 15, 2013.
International Search Report and Written Opinion for PCT Application No. PCT/US2012/029696 dated Apr. 4, 2013.
International Search Report and Written Opinion for PCT Application No. PCT/US2012/055797 dated May 28, 2013.
U.S. Appl. No. 13/424,170 , "Non final office action", dated Oct. 2, 2014, 29 pages.
U.S. Appl. No. 13/424,170 , "Notice of Allowance", dated May 27, 2015, 14 pages.
U.S. Appl. No. 13/536,935 , "Non-Final Office Action", dated Dec. 10, 2013, 7 pages.
U.S. Appl. No. 13/536,935, "Notice of Allowance," dated May 30, 2014, 7 pages.
U.S. Appl. No. 14/795,646, "Non-final Office Action," dated May 17, 2016, 6 pages.
U.S. Appl. No. 14/795,646, "Notice of Allowance," dated Aug. 9, 2016, 7 pages.
CN200880006903, "Communication from Chinese Patent Office", dated Aug. 24, 2011, 4 pages—English translation.
Department of the Navy , "Persistent Unmanned Autonomous Buoy", ONR/MTS Buoy Workshop 2006, Mar. 13, 2006, 21 pages.

* cited by examiner

AUTONOMOUS WAVE-POWERED VESSELS AND FLEETS FOR MANAGING FISH STOCK

RELATED APPLICATIONS

This application claims the priority benefit of U.S. provisional application 61/453,862, filed Mar. 17, 2011; and U.S. provisional application 61/502,279, filed Jul. 13, 2011.

This application is being filed contemporaneously with an application entitled "Wave-powered device with one or more tethers having one or more rigid sections" (Roger G. Hine), and and an application entitled "Wave-powered devices configured for nesting" (Roger G. Hine and Derek L. Hine), which are co-owned with this application by Liquid Robotics, Inc., Sunnyvale, Calif., U.S.A.

The aforelisted priority applications and contemporaneously filed applications, along with U.S. Pat. No. 7,371,136; U.S. Pat. No. 8,043,133; published applications US 2008/188150 A1; US 2008/299843 A1; WO/2008/109022; and provisional applications 61/535,116, 61/535,116, and 61/585,229 are hereby incorporated herein by reference in their entirety for all purposes.

FIELD OF THE INVENTION

The information disclosed and claimed below relates generally to the fields of global warming, vessel motility and control, and the biology of marine microorganisms. More specifically, it provides a system comprising wave-powered vessels that coordinate to fertilize plankton to improve the aquasphere and local fish population.

BACKGROUND

Global warming is an issue of considerable concern for mankind. The average surface temperature of the earth has increased by about 1.4° F., with about two thirds of the increase occurring since 1980. If the trend continues, severe consequences have been projected, such as melting of the polar ice caps, a rise in sea level, flooding of land below 50 feet in altitude, disruptive changes in weather patterns, and a severe impact on global ecology, with inevitable consequences for the human peoples. In view of the enormity and immediacy of the problem, new technologies are needed to reduce generation of greenhouse gasses such as $CO_2$, counter the effects, or remove greenhouse gasses from the atmosphere.

SUMMARY OF THE INVENTION

This invention provides a vessel system and methodology that can be used to promote growth of phytoplankton in the oceans. Unmanned self-controlled wave-powered vessels are equipped with storage units for dispensing a fertilizer, and with sensors to monitor ocean conditions and effects. Fleets of vessels move autonomously by on-board processing of GPS and directional information, piloting a path that is coordinated by a central processing unit. The vessels travel through a defined target area, creating a detailed survey of chemical and biological characteristics that affect grown. The data are processed in a computer model to identify precise locations and precise amounts of fertilizer that will produce the best results. Projected benefits of fertilizing plankton include sequestering $CO_2$ from the atmosphere, and enhancing the marine food chain to improve the fish stock in and around the treated area.

One aspect of the invention is an autonomous wave-powered substance distribution vessel. Components of the vessel include a vessel body, a steering means, a storage unit configured to release a substance into water in which the vessel is traveling; electronics configured to sense the geographical location of the vessel; and a microprocessor programmed to steer the vessel according to its location.

The storage unit on the substance distribution vessel may contain a fertilizer that promotes growth of phytoplankton and/or zooplankton, as described below, or a fish food. The storage unit optimally has a variable opening that is controllable to regulate dispensation of a substance contained in the storage unit into the water.

The vehicle may be constructed with a float traveling on the water surface, a swimmer traveling underneath, and one or more tethers connecting the float to the swimmer. The swimmer is weighted to travel in the water below the float, and is configured to pull the float by way of the tether. The swimmer has fin surfaces that mechanically provide forward thrust when actuated by rising and falling of the swimmer in the water. Other components of the vessel may include one or more sensors for determining a condition of water or air as listed below, and a microprocessor that adjusts release from the storage unit as appropriate.

Also provided as part of the invention are fleets that have several substance distribution vessels, plus several monitor vessels with one or more sensors. Besides on-board sensors, a monitor vessel may be equipped with an acoustic modem that receives data from a separate monitor positioned at a defined depth, or near the bottom of the body of water upon which the vessel is traveling.

The invention may be put into action by causing one or more substance distribution vessels to release a fertilizer in a target area. Typically, the substance is released from the vessels according to a condition of water or air as sensed by one or more monitor vessels. A substance such as a fertilizer may be distributed by causing a fleet of vessels to travel and monitor within a defined area; and release the substance within the area where appropriate.

Also provided is a central control unit for a water fertilization system. The control unit has a receiver for receiving information from each monitor vessel, such as its location and data obtained from one or more sensors aboard. The control unit also receives information from each substance distribution vessel about its geographical location. The control unit is programmed to process the sensor and location data, and make decisions about how much of the fertilizer is to be dispensed by the distribution vessels, and where they should travel. The vessels may communicate with a central control unit by satellite.

The invention also includes a water fertilization system that has a central control unit, monitoring vessels, substance distribution vessels, and electronics. The system receives information about each vehicle's location and provides instructions to the vehicles as to where to travel and where to distribute fertilizer.

Another aspect of the invention is a vessel that obtains electrical energy by wave motion. For example, the vessel may harvest the power of vertical movement using tethers attached to a spring-loaded suspension device. Wave energy is converted to potential energy in the springs, which is then used to drive an electricity generator. In another example, the vessel has a propeller that can be driven backwards as a generator when in motion so as produce electrical power. Electrical energy obtained by either of these means may be used to power electronics or stored in a battery for later use. The stored energy can be used to provide propulsion on calm days when wave action does not in itself provide enough power for the vessel to travel at the desired speed.

The various components of the invention may be put into action for the purpose of fertilizing plankton, feeding fish, promoting $O_2$ production, sequestering carbon from the atmosphere, or for any other application for which the components may be suitably adapted.

Further aspects of the invention will be evident from the description that follows.

BRIEF DESCRIPTION OF THE DRAWINGS

FIG. 4(A) is a side view; FIG. 4(B) is a perspective from above the left front side.

FIGS. 5(A) and 5(B) are sequential images of the configuration in action; FIG. 5(C) shows a detail of wave-generated potential energy in the springs to electrical power.

DETAILED DESCRIPTION

Fertilizing the Ocean to Combat Global Warming

A major contributor to global warming is carbon dioxide ($CO_2$). The concentration of $CO_2$ in the earth's atmosphere is about 392 ppm. Pre-industrial concentration was about 280 ppm, the level increasing almost exponentially with a growth rate of 2.2% per year in the last decade. The concern is heightened by the hypothesis that $CO_2$ has unique long-term effects on climate change that may be effectively irreversible. Solomon S et al., Proc. Natl. Acad. Sci. USA 106:1704-9, 2009. It has been estimated that to avoid dangerous climate change, a reduction of the $CO_2$ increase of 3.5% per year needs to be achieved Reducing $CO_2$ can in theory be done by lowering $CO_2$ emissions and by sequestering $CO_2$ that is already in the atmosphere A natural mechanism of $CO_2$ sequestration is incorporation of carbon by phytoplankton. These are microscopic organisms that inhabit the upper sunlit layer of almost all oceans and large bodies of fresh water. They create organic matter from $CO_2$ dissolved from the air, and become part of the food chain when consumed by zooplankton. A significant portion of the organic matter eventually ends up innocuously deposited on the seabed, and is thus effectively removed from both the atmosphere and the biosphere for decades or centuries.

It has been hypothesized that iron deficiency limits phytoplankton growth in some regions of the ocean, such as the Northeast Pacific Subarctic. J H Martin and S E Fitzwater, Nature 331:341-343, 1988. If this is true, iron fertilization (introduction of iron into the upper ocean) can be used to stimulate phytoplankton bloom. This in turn may enhance biological productivity, which can benefit marine life and remove $CO_2$ from the atmosphere.

However, there are both economic and ecological concerns that have prevented iron fertilization of the ocean from being practiced on a large scale.

Current trials use large ships to deliver the fertilizer or large pipelines to pump fertilizers from the shore. These distribution methods are expensive, both in terms of the fuel consumed, and the cost of manning the ships and pipelines. Monitoring the effects of fertilization from naval vessels implicates a further layer of fuel consumption and human resources. Besides the cost, the added fuel consumption adds more $CO_2$ into the atmosphere, countering the beneficial effect of the fertilization. Furthermore, overfertilization of an area of the sea risks the growth of unwanted organisms, adversely affecting the balance of species.

The invention described here provides a system that can be used to fertilize phytoplankton on a large scale, in a way that is highly controlled, highly monitored, and runs on naturally supplied energy. Benefits of the invention include the following:

A cost-effective means of monitoring a wide variety of possible effects for long time period. The monitoring vessels may be programmed or controlled to remain in a particular area, or they may follow ocean currents and effects, moving to various locations as needed.

Measured release of fertilizer that can be accelerated, slowed or stopped in response to data received from the monitors.

The ability to perform both monitoring and fertilizer delivery far from population centers or sensitive coastal zones. Such locations otherwise may be commercially impractical because of accessibility and the costs of sending manned ships to distant sites.

The ability to limit waste of fertilizer, and thus limit unnecessary deleterious effects of overfertilization on the environment.

The ability to control fertilizer distribution in an exquisitely sensitive fashion, fertilizing at optimal times and optical locations selected on an ongoing basis, and not limited by the constraints of a ship's fuel supply or crew time.

Scalability and adaptability, enabling widely dispersed or remotely located fertilization as an option to reduce the risk of possible harmful effects.

Fertilization Strategy of the Invention

Projected benefits of fertilizing plankton in the ocean include not only $CO_2$ sequestration, but also a bottom-up feeding of the food chain. The fertilizing strategy can be designed with an eye to improving aquaculture in the ocean, and the harvestable yield of larger marine organisms.

The systems and methodologies of this invention are built on the idea of using vessels that both navigate and are powered autonomously. Self-guiding vessels can be deployed in a region of the ocean at considerably lower cost than can be achieved with manned watercraft. The water and growth conditions are surveyed throughout the area at multiple locations on a continual basis. The compiled data enables vessels to dispense very precise amounts of fertilizer at precise locations in the area, fine tuning the distribution as conditions change.

Figure 1:
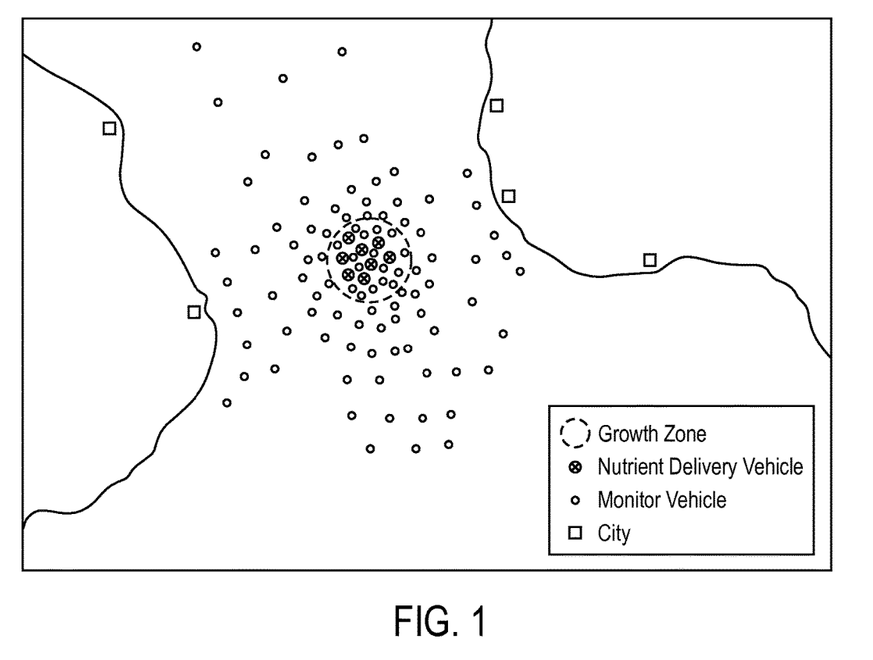
FIG. 1 is a map showing a fleet of vessels that are distributing fertilizer to a target growth zone in between two coastlines. In this illustration, the vessels are wave-powered and unmanned. Monitor vessels have sensors that determine conditions of the air and/or the water in and around the target zone. The information is then transmitted to a central control unit which may be on one of the vessels, or ashore. The control unit processes the data to determine where and how much fertilizer should be distributed to obtain the desired results. Nutrient delivery vessels are then instructed by the control unit to distribute the fertilizer where needed

FIG. 1 provides an illustrative model of how the technology of this invention can be deployed. Shown is an ocean strait passing between coastlines on the left and right side. In this illustration, a fleet of autonomous vessels is being coordinated to improve plankton growth in the zone marked in the middle. Monitor vehicles travel within and around the target zone, monitoring chemical and biological conditions related to fertilization activity. Based on the data collected, nutrient delivery vehicles are positioned at optimal locations and commanded to dispense an optimal amount of fertilizer as the need arises. Improved plankton growth drives the food chain, thereby increasing fish stock for the benefit of fishing communities in cities and towns on nearby coastlines.

Autonomous Wave-Powered Vessels

The distribution strategy of this invention is typically put into action using watercraft of which all or at least a majority are typically autonomous vessels. Each vessel self-navigates and performs its stated function without needing a human on board. It is also autonomous in the sense that it has its own source of power—such as a long lived battery, or a motor requiring minimal fuel—or it obtains its power in the course of its operation from natural sources: in particular, wind power, solar power, or power derived from the movement of waves. Any vessel used in the context of this invention may have any one or any combination of such power sources, unless a particular power source or combination is indicated.

The use of wave power is well suited to this invention, because the motion of the waves can be mechanically translated into locomotive force for the vessel, without converting the power source to electricity as an intermediate. Prototype vessels obtain at least 75%, 90%, 95%, or 100% of their locomotive power from wave motion, and obtain power to run electronics from photovoltaic cells displayed upwards on the portion of the vessel that travels along the surface.

Figure 2:
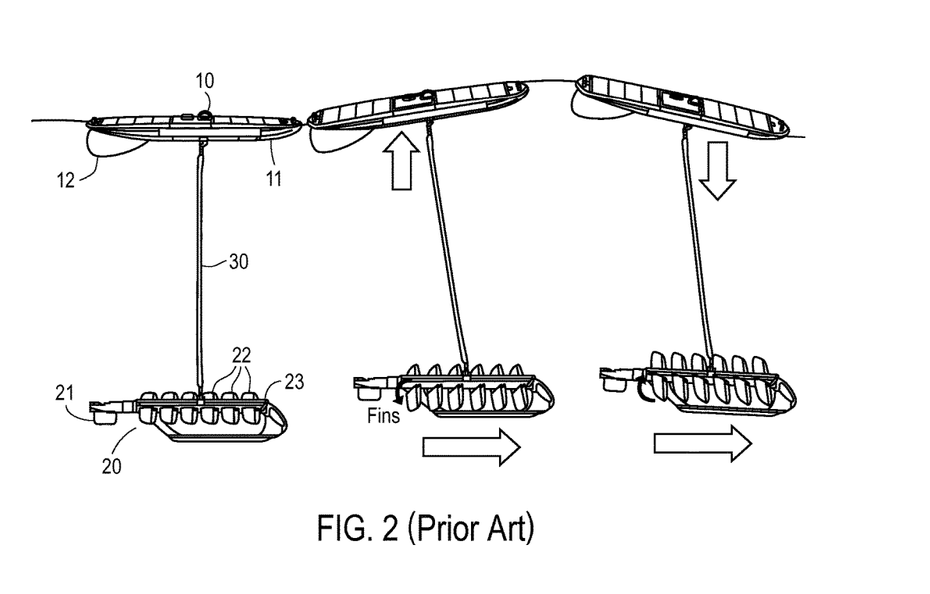
FIG. 2 is a side perspective of three images of a wave-powered vessel, showing how vertical movement of the waves can be harvested to provide the vessel with locomotive power.

FIG. 2 is a side view of a wave-powered vehicle that may be adapted in accordance with this invention. The vehicle comprises a "float" 10 resting on the water surface, and a "swimmer" or "glider" 20 hanging below, suspended by a tether 30. The float 10 comprises a displacement hull 11 and a fixed keel fin 12. The swimmer comprises a rudder 21 for steering and "wings" or "fins" 22 connected to a central beam of the rack 23 so as to permit rotation of the wings around a transverse axis within a constrained range, and provide propulsion.

In still water (shown in the leftmost panel), the submerged swimmer 20 hangs level by way of the tether 30 directly below the float 10. As a wave lifts the float 10 (middle panel), an upwards force is generated on the tether 30, pulling the swimmer 20 upwards through the water. This causers the wings 22 of the swimmer to rotate about a transverse axis were the wings are connected to the rack 23, and assume a downwards sloping position. As the water is forced downward through the swimmer, the downwards sloping wings generate forward thrust, and the swimmer pulls the float forward. After the wave crests (rightmost panel), the float descends into a trough. The swimmer also sinks, since it is heavier than water, keeping tension on the tether. The wings rotate about the transverse axis the other way, assuming an upwards sloping position. As the water is forced upwards through the swimmer, the upwards sloping wings generate forward thrust, and the swimmer again pulls the float forwards.

Thus, the swimmer generates thrust when both ascending and descending, resulting in forward motion of the entire craft.

A wave-powered vessel suitable for use in this invention may be described as comprising the following components: a float; a tether secured to the float (which can assume an adjacent position relatively close to the float, or an extended position extended below the float), and a wave-actuated component (a swimmer with fins) that is secured to the tether. The float, the tether, and the wave-actuated component are configured so that when the device is in still water and the tether is in the extended position, the float is positioned on or near the surface of the water, and the tether and the wave-actuated component are submerged below the float. When the device is in wave-bearing water and the tether is in the extended position, the wave-actuated component interacts with the water to generate forces that are transmitted to the tether, thereby pulling the float and providing propulsion and locomotive power to the vessel as a whole.

Navigation

A vessel may navigate autonomously by having a means of determining the geographical location of the vessel, a means for determining direction, a means for steering the vessel, and a means of operating the steering so that the vessel travels or stays at a target location. The steering means may be a rudder that turns sideways against the water so as to cause the vessel to spin towards a new heading. Alternatively or in addition, it may be a mechanical arrangement that presses upwards and downwards on opposite sides of the vessel in the manner of an aileron, thereby causing the vessel to roll sideways and attain a new heading. Where the vessel comprises a surface component and an underwater component (such as in FIG. 2), a steering means may be mounted on either component.

Electronics to sense the geographical location of a vessel can triangulate off a series of reference points. Particularly effective is the global positioning system (GPS), or a similar network of positional transmitting sources. The vessel will also usually have an electronic compass or gyroscope to determine the vessel heading. Positional data about the geographical location and the vessel heading is processed in a decision algorithm or programmed microprocessor, which may then provide navigation instructions. Consequently, the steering means adjusts to head the vessel in accordance with the instructions.

Figure 3:
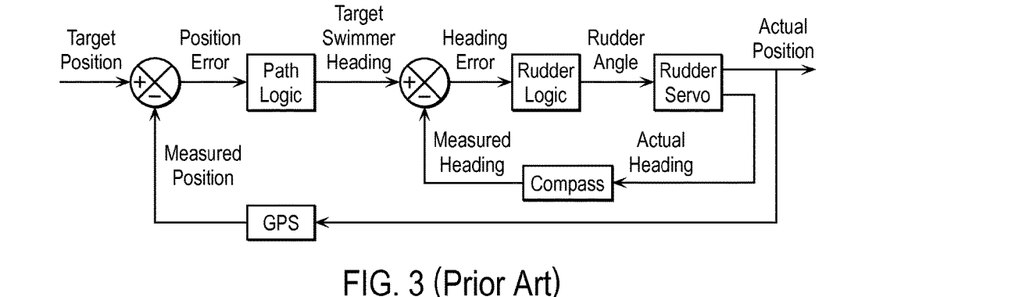
FIG. 3 is an algorithm used by an unmanned vessel to pilot a course to a target position using data from a GPS receiver and a compass.

FIG. 3 shows an example of an algorithm for directing a vessel towards or maintaining it at a target position (a geographical location). Once the target position is inputted, it is compared with the current location of the vessel inputted from a GPS receiver. The processor calculates the proper heading, and compares it with the heading inputted from the compass. The processor then outputs instructions to the rudder servo to adjust the vessel onto the correct heading. For vessels that are capable of regulating transit speed or locomotive force, the processor may also output instructions to adjust the speed (not shown). Measurement and correction by comparison with GPS and compass data is performed iteratively as the journey continues.

Autonomous wave-powered vessels that can be used in this invention are described in further detail in U.S. Pat. No.

7,371,136; U.S. Pat. No. 8,043,133; and published applications US 2008/188150 A1; US 2008/299843 A1; and WO/2008/109022. Exemplary vessels are manufactured and sold by Liquid Robotics, Inc., Sunnyvale, Calif., USA under the brand Wave Glider™.

Vessels Powered by Both Wave Motion and Solar Energy

This disclosure provides as an option a new multipowered autonomous energy-harvesting vessel that can be deployed as part of a monitoring and fertilizing fleet, and also in other contexts where an autonomously powered vessels can be adapted to perform the desired activity.

The new vessel has two sources of power. One is wave power as already described, wherein vertical movement of the vessel is mechanically converted into a locomotive force to drive the vessel through the water horizontally. As a novel feature, the vessel also converts part of the wave energy to electrical power, wherein passage of the vessel through the water drives a turbine-coupled generator. A second source of power is solar energy, which feeds electricity into the same electrical system by way of photovoltaic cells mounted on a horizontal or upward facing part of the vessel body.

The electrical energy from either source can be stored in an on-board rechargeable battery. Electrical energy obtained from solar power, from the turbine-coupled generator, or from the battery can be used to power on-board electronics and microprocessors. It can also be used to power an electrically driven propulsion system, such as an electric motor coupled to a propeller or turbine. Thus, on calm days when there is insufficient wave motion to drive the vessel at the desired speed, the battery and the photovoltaic cells can power the propulsion system. Conversely, the wave generated electrical power can be stored for use during periods that are too dark to rely entirely on solar power—for example, at night.

Figure 4A:
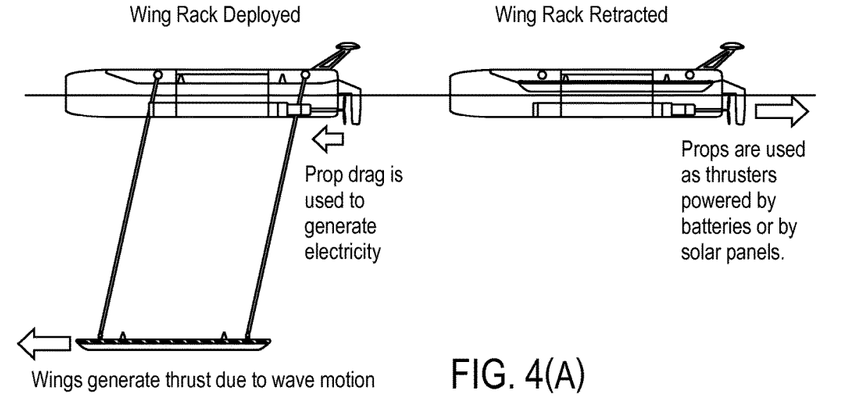
FIGS. 4(A) and 4(B) show side views of another wave-powered vessel. It has a propeller that can be turned one way to provide propulsion, or the other way to generate electricity.
Figure 4B:
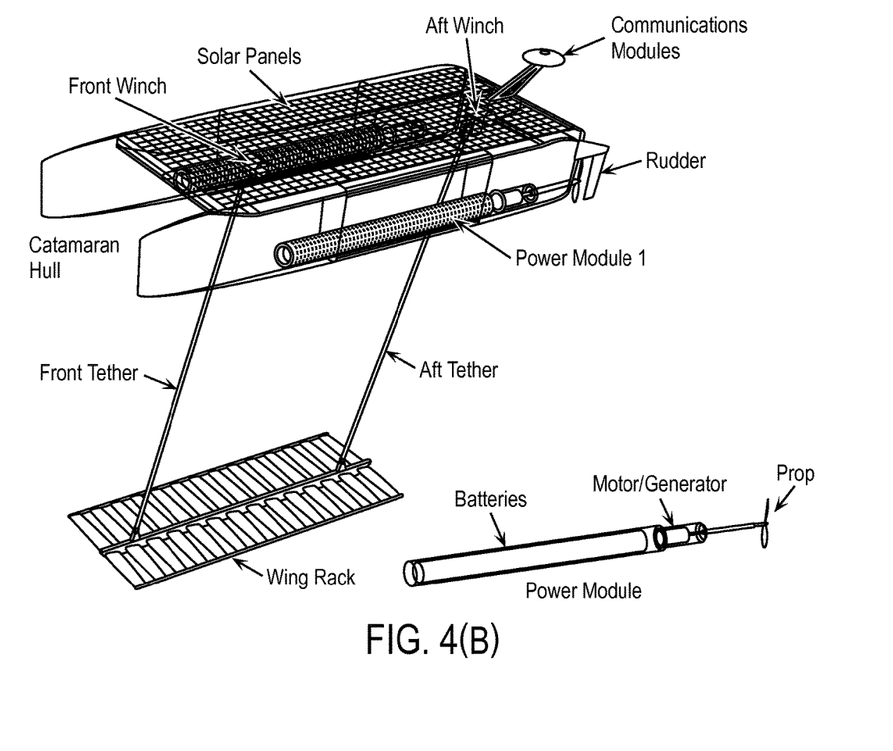

FIGS. 4(A) and 4(B) show an example of an autonomous vessel that is principally driven by wave power, and also has auxiliary solar power. In this example, the swimmer or wing-rack is tethered to the buoy or vessel body by a foreword and aft tether with a winch for adjusting the length of tether that is deployed. As the buoy moves up and down with the waves, the swimmer rack has wings that translate the vertical movement into transverse locomotive movement. The wing-rack then pulls the vessel body as directed by the rudder under control of the microprocessor.

The electrical system comprises the upward facing solar panels, and the power module shown in the inset to FIG. 4(B). The power model comprises rechargeable batteries, a second component that plays the role of both motor and generator, and a third component that plays the role of both propeller and turbine. As shown in FIG. 4(A), when there is an abundance of wave power, the wings on the swimmer generate thrust or locomotive power to move the vessel forwards. As the waves power the vessel through the water, the propeller is turned backwards, applying torque to the motor so as to generate electrical power for storage in the battery. When there is an absence of wind power, or when the wing rack is retracted into the vessel body, the batteries or solar panel powers the motor, which turns the propeller so as to provide locomotive power.

In the configuration illustrated in the figure, six SunPower™ E20 panels each containing 96 cells are mounted to the top deck. The panels use 22% efficient Maxeon™ cells for a maximum power output of 327 Watts measured at standard test conditions: irradiance of 1000 Watts/m$^2$, AM 1.5, and cell temperature of 25° C. Under these conditions, the panels produce 1962 Watts.

Vessels that Use Wave Power for Both Locomotion and Generation of Electric Power As an alternative or in addition to generating electrical energy from horizontal movement of the vessel, an electrical generator can be driven by vertical movement of the vessel caused by the waves. The autonomous vessel is configured so that the vertical undulations of the vessel are mechanically coupled to a means of providing horizontal locomotive power to the vessel (such as a fin or wing rack), and are also mechanically coupled to a generator of electrical power.

In vessels equipped in this way, other sources of power or electricity (like photovoltaic cells for solar power) are entirely optional—the wave motion mechanically provides power to drive the vessel through the water, and also provides electricity to run electronics and microprocessors aboard. If there is electrical power in excess of immediate needs, it can be stored in a rechargeable battery. The stored electrical power can be used to power electronics or provide locomotive power to the vessel (for example, by way of a propeller) at times when wave motion is not sufficient to provide immediate needs.

Figure 5A:
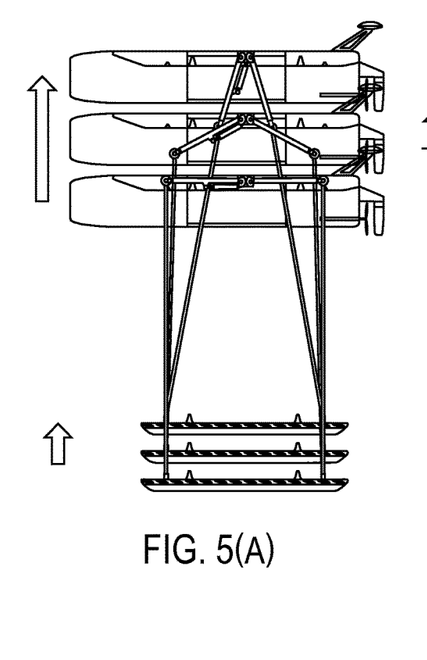
FIGS. 5(A), 5(B), and 5(C) provide superimposed images of a vessel harvesting vertical wave motion to generate electricity.
Figure 5B:
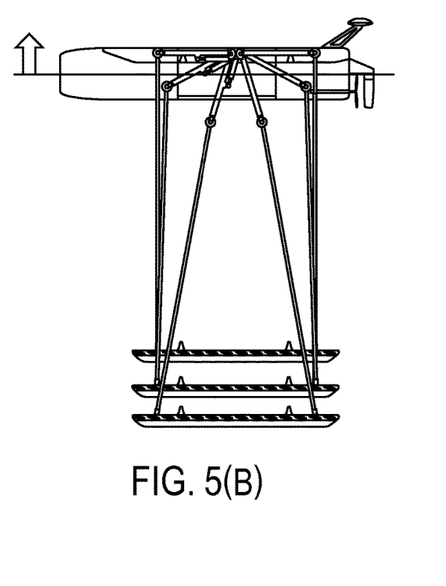
Figure 5C:
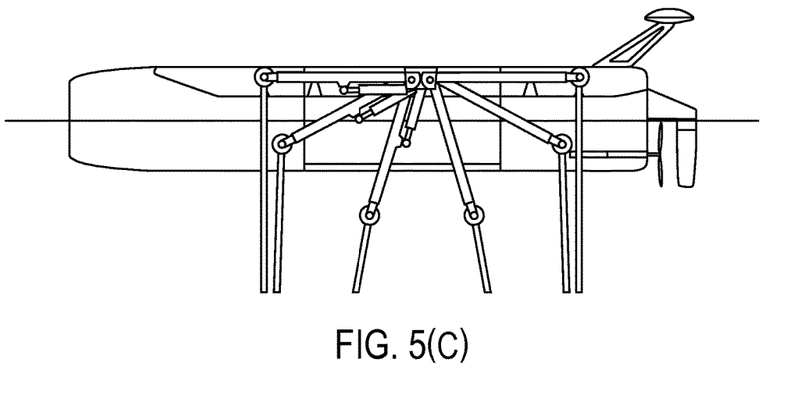

FIGS. 5(A), 5(B), and 5(C) are side views of an autonomous wave-powered vessel comprising a buoy and a swimmer. The vessel has been equipped to harvest wave motion for both locomotive and electrical power. There are two tethers connecting the buoy to the swimmer, fastened to opposite arms of a suspension device. The arms of the suspension are spring loaded to return to a neutral horizontal configuration in opposite directions along an axis parallel to the vessel's length, pivoting around a central suspension point.

FIG. 5(A) superimposes three images showing what happens when the buoy is lifted by a wave. At the starting position, the suspension device is configured in the neutral position with arms horizontally positioned in opposite direction. As the wave lifts the boat, the boat pulls the swimmer upwards. However, since the density of water slows the upward movement of the swimmer, thereby pulling the arms of the suspension device downwards (top image). This loads the spring on each arm with potential energy.

FIG. 5(B) superimposes three images showing what happens as the vessel approaches the crest of the wave. The upwards motion of the float slows, but the swimmer still travels upwards due to the tension in the arms when they are pulled downward. As the swimmer continues upwards to a point where the arms resume the neutral horizontal position, the potential energy in the suspension device is released, and can be captured by a generator means that converts the potential energy in the spring into electrical power.

FIG. 5(C) superimposes three images of the configuration of the suspension device as the potential energy is released. In this example, the two tether winches pivotally mounted to the ends of link-arms drive a linear hydraulic cylinder, which in turn creates pressure to drive a hydraulic turbine generator. The link arms could package nicely in the center span structure without protruding above the solar deck. Optionally, the link arms could be configured to lock in the neutral horizontal position during times where all of the wave energy is needed for thrust, or when electric generation is not necessary.

Substance Distribution Vessels that can Carry Fertilizer

In order for an autonomous vessel to distribute fertilizer or another substance at a target site on a body of water, the vessel is equipped with a storage unit or container that is configured to release a substance into water in which the vessel is traveling. The storage unit may be integral to the vessel, pulled along the surface in the manner of a barge, or pulled through the water below the surface as a submarine tow body.

The storage unit will have a variable opening that is controllable to regulate dispensation of the substance contained in the storage unit as the vessel travels through the water. Different amounts of the substance can be dispensed by adjusting the amount of the opening. Alternatively, the opening may be configured to dispense the substance into the water as boluses having the same size or weight. Thus, the amount of substance can be varied by counting the number of boluses that are released. The storage unit may be configured and operated to dispense the desired amount once the vessel has completed its journey to a target location. The storage unit may also be configured and operated to dispense the substance at a variable controlled rate as the vessel is traveling.

Figure 6:
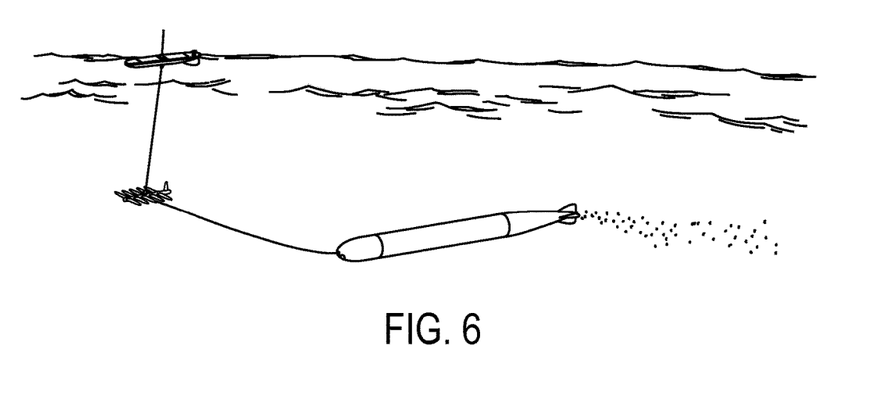
FIG. 6 depicts a wave-powered distribution vessel pulling an underwater storage unit dispensing fertilizer.

FIG. 6 depicts a wave-powered vessel towing a submerged nutrient storage and distribution container with fertilizer particles being distributed into the ocean from the tail of the container. In this example, the container is a tow body being pulled by the wing rack of the vessel. The benefit of using an underwater storage unit is that it is protected from surface wind and waves. There is also less drag, because surface boats produce waves that cause additional drag compared with an underwater distribution container having the same displacement volume.

A submerged container can be configured to maintain neutral buoyancy as it distributes fertilizer. This can be done by providing the storage unit with an air chamber that gradually floods as the fertilizer is released. For example, a valve opening may be located near the front of the storage unit and another at the tail. When both valves are open, water will flow through the chamber in which the fertilizer is stored, mix with the fertilizer, and flow out the tail opening. Thus, the volume of the fertilizer released will be replaced as a matter of course by a corresponding volume of water on an ongoing basis. Alternatively, a fertilizer mix can be used that has neutral buoyancy at the depth of travel.

In addition to adjusting the weight of the storage unit, active buoyancy stabilizers can be installed on the storage unit to trim the buoyancy and maintain desired depth: for example, an adjustable hinged flap on either side. The stabilizer works in the manner of an aircraft elevator to adjust the pitch of the storage unit, thereby adjusting its tendency to travel downwards or upwards to a neutral substantially horizontal position.

The shape of a submarine container can be optimized to have minimal fluid drag when pulled by the vessel. For example, a 12 metric ton (27,000 pound) displacement hull that is 6 m long, 1.7 m in diameter, and hydrodynamically shaped would require only about 8.25 N (about 2 pounds) of thrust to move at 0.5 knot. A relatively small wave-powered vessel can easily produce this amount of thrust in most ocean conditions. For example, the present model Wave Glider™ could tow such a submerged and neutrally buoyant container consistently at 0.5 knot, and would often be able to achieve 1 knot.

Rather than using a submerged container, the vessel can be equipped with a storage unit that carries and distributes the fertilizer at the water surface. For example, a storage unit could be towed as a barge, or the storage unit could be built into the vessel body or float. A surface barge may be more susceptible to damage from severe weather. Use of a submerged container is often preferred, because it is protected from the wind, and wind generated surface currents are greatly reduced at a depth of only a few meters. Another option is to fashion the vessel body and/or the swimmer with an internal storage unit and a means for dispensing a substance such as fertilizer into the water.

Monitor Vessels that Carry Sensors

For an autonomous vessel to play the role of a monitor vessel, it is equipped with one or more sensors to determine a condition or characteristic of the water and/or the air around and about the vessel.

Sensors and related equipment that may be used on the monitor vessels of this invention include one or more of the following in any suitable combination:

Sensors of $CO_2$ concentrations in air, and water, and/or $CO_2$ flux

Sensors of oxygen concentrations in air and water and/or oxygen flux

Heat flux sensors

Meteorological sensors; wind speed & direction, air temperature, solar intensity, rain fall, humidity, pressure Physical oceanography sensors; wave spectrum & direction, current sensors, CTD profiles Micro-organism counts and classification through water sampling and vision systems Fish and wildlife tracking by acoustic tag detection, such as those manufactured by Vemco FAD structures to provide shade and attract marine life Acoustic sensors for active or passive detection and classification of marine wildlife. For example, hydrophone for listening to whales, or active sonar for fish counts Chemical sensors to detect the concentration of the fertilizer being released Large organisms can be counted and classified by way of vision systems. They may be configured to detect motion and store data in response to detection. Image and video data is transmitted via satellite or line of site radio to control centers on ships or shore. Data may be used to count fish numbers and types. Still images or video may be captured above surface, to see weather, above water life, and possibly for security functions.

The vessel may also carry optical or chemical sensors to characterize the desired growth of phytoplankton. Such sensors may also detect possible adverse effects of fertilization, such as harmful algal blooms. Such sensors may be selected from a conductivity-temperature-depth sensor, a fluorimeter, a transmissometer, a nephelometer, a bioluminescence detector, an irradiance meter, a nitrate/nitrate sensor, and a plankton sampler.

Equipment installed on a vessel of this invention to facilitate data collection may include a means for obtaining sensor data at variable depths. This can be achieved using a winch system to lower and raise sensors mounted on a heavier-than-water platform. Another options a tow-body mounted with sensors, with servo-controlled elevator fins to alter the pitch of the tow body, thereby controlling its depth while being pulled. The vessel may also have data storage systems and a microprocessor programmed to process and interpret data from the sensors, either integrated into the location and navigation processing and control system on the vessel, or as a stand-alone microprocessor system.

Figure 7:
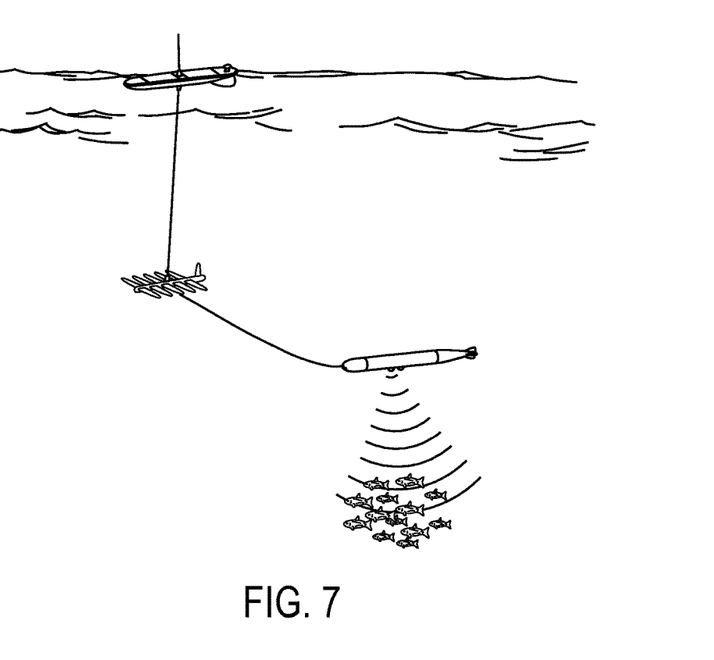
FIG. 7 depicts a wave-powered vessel pulling an underwater tow body that has sensors for monitoring fish.

FIG. 7 shows an autonomous wave-powered monitor vessel in which one or more of the sensors are located on tow body being pulled behind the vessel. The tow body may or may not be the same body used for distributing a substance into the water as shown in FIG. 6. The sensors can be connected through the tow line to the microprocessor and transmitter in the vessel body, or connected to a transmitter on the tow body that transmit data directly to another vessel or control center. The sensor depicted here is active sonar for imaging schools of fish and other marine life.

Ocean currents affect distribution of fertilizer in the target area. A vessel of invention may have current measurement equipment such as Acoustic Doppler Current Profilers. The vessel itself may be used to measure currents by performing navigation maneuvers designed for this purpose. The vessel may deactivate thrust generation and simply drift, or control the direction of thrust generation such that current can be inferred from the vessel's path determined by GPS. The net motion of the vessel reflects the effect of the current averaged over that time period and area. Fertilizer release from vessels may take into account the current so as to achieve the desired concentration levels and evenness of distribution over an area.

Dual purpose vessels can be equipped with one or more sensors, as described here, plus a fertilizer storage unit, as described earlier. Such vessels may be programmed to act on their own, alternately or simultaneously monitoring an area targeted for fertilization, and dispensing fertilizer from the storage unit. Vessels that have both functions and operate on their own typically are programmed with locating, navigating, mapping, forecasting, and modeling algorithms that are characteristic of a central control unit, as described below. Alternatively, dual purpose vessels can be part of a fleet for dispensing fertilizer as shown in FIG. 1, where they may play the role of a monitoring vessel, a substance distribution vessel, or both.

Other Types of Monitoring

Besides sensors located on monitor vessels of the fleet, the fertilizer distribution system may also comprise one or more monitors located elsewhere. For example, temperature, air quality, and image sensors can be located on land within or near the target area. Sensors can also be deployed at fixed positions within the body of water: for example, on the bottom, or suspended from a fixed buoy or float at a defined depth by way of a tether. In planning and monitoring a fertilization distribution strategy, it may be helpful to measure the amount of carbon containing detritus that settles on the sea bottom in the target area as a proxy of $CO_2$ sequestration, other effects on water chemistry, or the effect on marine life. The data from a remote sensor can be transmitted directly to a vessel or control unit, or by relay.

Figure 8:
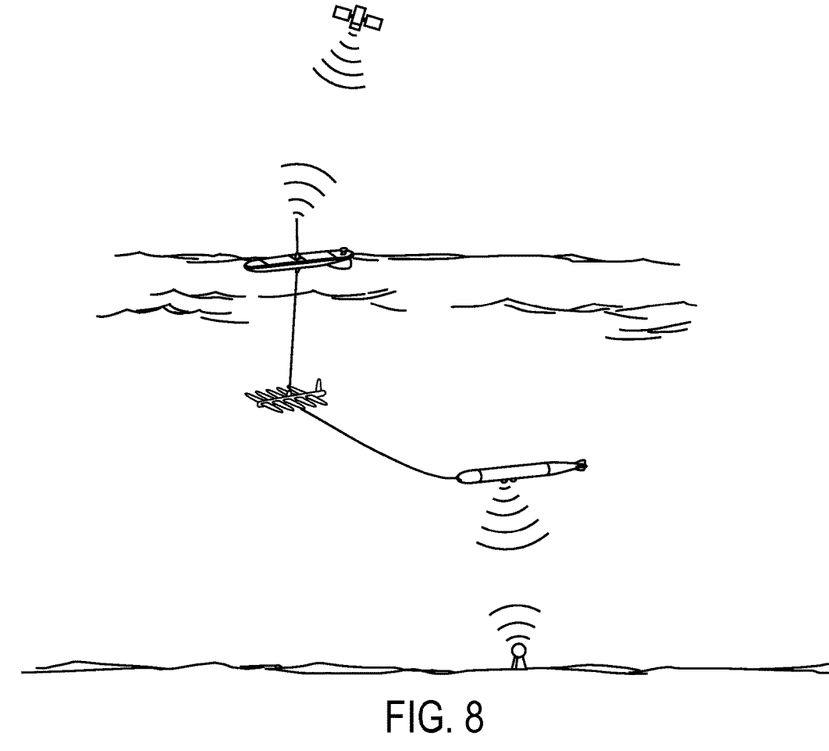
FIG. 8 depicts a monitor vessel receiving data from a sensor located on the sea floor, and transmitting the data to a control unit by satellite.

FIG. 8 depicts an arrangement in which a wave-powered monitoring vessel pulls a tow buoy that carries an acoustical modem. This enables the monitoring vessel to receive data from a separate monitor unit positioned at a defined depth, or near the bottom of the body of water upon which the vessel is traveling. The data is then conveyed to a vessel-bound processor or central control unit for processing and interpretation. The monitor will have one or more sensors for determining data related to fertilization activity—for example, a sensor that measures $CO_2$, a fish counting sonar, an acoustic fish tag receiver, an acoustic Doppler current profiler, or a water quality sensor.

The Central Control Unit

This invention also provides a control unit that can perform centralized processing of sensor data and navigation instructions. The control unit receives information about the geographical locations of vessels in the fleet that the vessels determine using their GPS system. It also receives data pertaining one or more conditions of the water or air from monitor vessels. The control unit compiles the data, and applies an algorithm to make decisions about where it is appropriate to distribute fertilizer or another substance from the distribution vessels. It then sends instructions to each distribution vessel for navigation and/or distribution: for example, to distribute a certain amount fertilizer at the vessel's current location, or to travel to another location where fertilizer is needed.

Figure 9:
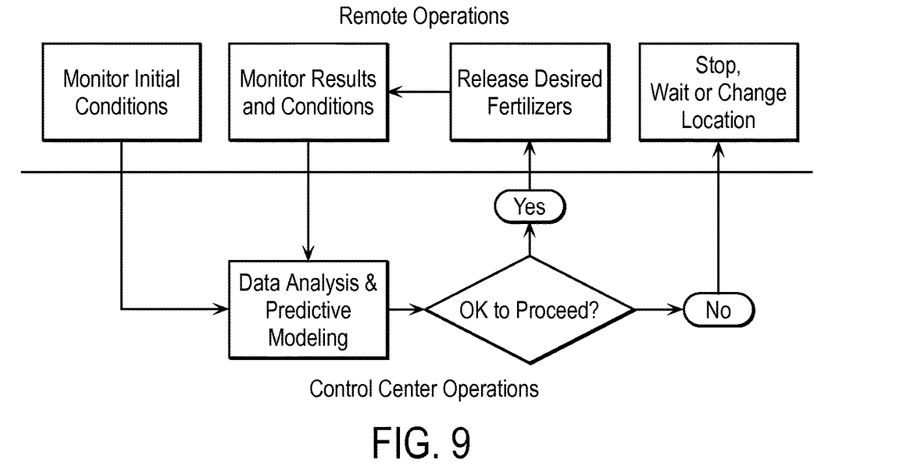
FIG. 9 is an algorithm that enables a control center to receive sensor data and instruct a fleet of vessels on where to distribute fertilizer.

FIG. 9 shows a basic algorithm by which a central control unit may manage vessels in the fleet. Functions performed by the vessels are shown above the horizontal line, and functions performed by the control unit are shown below the line.

Monitor vessels are sent to determine initial conditions, and report back to the control unit. Analysis and modeling of the data by the control unit determines whether it is appropriate to proceed with distribution of fertilizer at the present location of each of the dispensing vessels. This leads to a cycle where monitor vessels reassess conditions in the target area, the control unit makes a corresponding adjustment to the model, and an assessment is made as to whether fertilizer is needed at the same or a different location for each of the dispensing vessels. Both the monitoring vessels and the dispensing vessels can be commanded to change their location in accordance with the evolving model. Typically, the command unit will direct each of the vessels to a specific new location (not shown). The vessels can then self-pilot to the new location using an on-board navigation algorithm of the nature shown in FIG. 3.

The control unit typically operates most of the time without human decision making, but within parameters programmed or provided by and periodically adjusted by human operators. Such parameters include defining the target area, setting the objective end-point, and placing limits on various activities and effects. The control unit may be placed anywhere on shore within range to receive and transmit data and instructions to the monitor and substance distribution vessels under its control. It may be aboard an autonomous vessel or manned ship that is separate from the substance distribution and monitoring vessels in the fleet. Alternatively, it may be aboard one of the monitor vessels or substance distribution vessels, optionally integrated with the microcircuitry and programming of that vessel.

FIG. 8 shows a monitor vessel pulling a tow body that has a modem to receive data from a separate underwater monitoring unit. The data is then conveyed to the transmitter on the vessel that communicates with other vessels and/or a control unit via satellite. In general, the vessels in the fleet and the control unit may communicate to each other by any suitable wireless technology.

The use of a satellite mediated communication system allows the vessel fleet to travel or be deployed to locations at any distance from the control unit around the globe. This enables fertilization to occur in regions that may be hard to get to, such as the Antarctic. It also enables the control unit to be placed at any location that is convenient to persons involved in programming or setting operating parameters for the fertilization system. Thus, the control unit can be placed on a manned vessel operating near the area targeted for fertilization, or it can be located anywhere on shore.

Choice of Fertilizer and Formulation

Fertilizer can be selected and distributed according to this invention the purpose of promoting the growth of plankton or other marine organisms. In areas of the ocean where an essential nutrient for plankton are sufficiently low to be growth limiting, it is often possible to promote growth by supplementing the nutrient availability.

A low concentration of iron in some ocean areas may be limiting plankton growth. J H Martin, Paleoceanography 5:1-13, 1990. Accordingly, there is considerable potential in using iron as a fertilizer to stimulate phytoplankton bloom.

There is also evidence that away from the coastal waters, much of the ocean is a desert, being deficient in the nitrogen needed for phytoplankton growth. The supplementation of nitrogen in these the ocean waters may increase the production of phytoplankton. ISF Jones and H E Young, Environmental Conservation 24:99-104, 1997. This supports use of a fertilizer that comprises a nitrogen containing organic compound such as urea. Other ocean solutes and micronutrients that may have a fertilizing effect for plankton under certain conditions include phosphorus. T M Lenton and N E Vaughan, Atmos. Chem. Phys. Discuss. 9:2559-2608, 2009.

Active agents of a fertilizer may be formulated by combining with carriers or other excipients that assist in the storage, granularity, distributability, releasability, bioavailability, and/or stability of the active agents once distributed into the water. Convenient forms for distribution are solid ablative forms that release fertilizer into the water, soluble particulates, and liquids in which the active agents are dissolved. Particles may be coated with an inert protective layer for delayed or timed release after distribution. The fertilizer may contain particles that have a buoyant portion coupled with the heavier active portion, such that the combined particles float in the eutrophic zone (the top 100 meters where microorganisms perform photosynthesis) to support the growth of phytoplankton.

Fish Farming

Distribution of fertilizers for plankton initiates the food chain, which can ultimately lead to a greater food supply for fish, thereby increasing populations of fish near the fertilized area.

Another way to promote production of fish in accordance with this invention is to distribute food for flora or fauna further up the food chain, including to the fish directly. The food is distributed in a region that has suitable living conditions for fish and a starting population of the desired species. Pellets or powders containing food palatable and nutritious to fish may be loaded into a storage unit on a substance dispensing vessel, and distributed to target regions as already described to promote the growth of fish. Monitor vessels, if they are employed, can comprise sensors to detect an identifying ingredient of the fish food, and imaging and counting equipment for fish of the desired size.

Fish feeds made on a large scale are typically produced by grinding and mixing together ingredients such as fishmeal, vegetable proteins and binding agents such as wheat. Water is added and the resulting paste is extruded through holes in a metal plate, and cut to form pellets of the desired size. The pellets are dried and oils are added. Fish feeds for aquaculture are commercially available from the Biomar Group and the EWOS Group.

Fertilization of plankton or direct fish feeding may be combined with caged aquaculture to reduce the need for food being brought in externally to feed the caged fish. The fertilization may be done in deep water far off shore where there will be minimal impact on ecosystems. It may be done to increase fish populations nearer to a coastline, for the benefit of a local fishing community.

Fish farming according to the invention may be practiced in a particular area of the ocean off-shore, in a confined bay or estuary, or in a land-locked body of water, such as a sea, lake, or pond. It may be done in a publicly accessible body of water for the general benefit of the community, or in a defined body of water that is dedicated to commercial fish farming.

Glossary

The terms "vessel" and [sea going] "vehicle" are used interchangeably in this disclosure and the priority documents to refer to a nautical craft that can travel across and about any body of water at or near the surface.

A "wave-powered" vessel is a vessel that derives at least a majority of its power for locomotion from motion of the water in relation to the surface. Optionally, the vessel may also derive power from solar energy and other natural sources, and/or man-made sources such as batteries and liquid fuel powered engines. In this context, a "wave" is any upward and downward motion of the surface of a body of water at a point of reference (such as the center of floatation of a vessel).

A "swimmer" is a component of a vessel that travels below the surface of the water and pulls or provides locomotive power or propulsion to another component of a vessel, such as a float.

A "float" is a component of a vessel that travels on or near the surface of the water. It may have its own source of locomotive power. In the two-component vessels illustrated here, the float plays a passive role and is pulled by one or more swimmers.

A "vessel body" is the largest component of a vessel that is configured to travel across a body of water. Other components tethered to or pulled by the vessel body may be referred to in this disclosure as part of the same vessel. In embodiments of the invention where a vessel comprises both a swimmer and a float, the vessel body is the float.

An "autonomous" vessel is a vessel that is designed and configured to travel across a body of water without needing a human on board or in constant active control at a remote location. It has a self-contained source of locomotive power. Navigation is controlled, either by a combination of sensors, electronics, and microprocessors aboard or at a remote location and in wireless communication with the vessel. It is not necessarily wave-powered, unless so indicated or implied.

A "Wave Glider™ is any of a family of exemplary autonomous wave-powered vessels manufactured and sold by Liquid Robotics, Inc. in Sunnyvale, Calif., USA. Current models have a float, and one or more swimmers or fin racks, with one or two tethers that connect the swimmers to the float so as to provide locomotive power to the vessel. Reference to the Wave Glider in this disclosure and the priority documents illustrates a structure, function, adaptation, are use that may more generally be applied to other autonomous vessels.

A "microprocessor" or "computer processor" on a vessel or control unit of the invention inputs data, processes it, and then provides output such as data interpretation or instructions to direct the activity of another apparatus or component. For vessels or units that have different data sets for processing in different ways, the microprocessor for each algorithm may be separate, but more commonly they are a single microprocessor configured and programmed to process each the different data sets with the corresponding algorithms when it is appropriate A "[substance] distribution" vessel or vehicle is a vessel equipped to distribute a substance into or over the water in which it is travelling. The vessel will typically have an internal or a hauled storage unit containing the substance, with a port that can be regulated to control distribution of the substance at particular rates and in particular locations. The distribution may occur as a bolus or series of boluses, or as a continual release. The "substance" may be any liquid, particulate or dissolvable solid that the user wishes to distribute in a body of water in accordance with this invention. Depending on the context, the substance being distributed may but does not necessarily comprise a fertilizer.

A "fertilizer vessel" or a "nutrient delivery" vessel is a substance distribution vessel that either contains or has been configured to carry fertilizer.

A "storage unit" is a chamber that is part of or pulled by a vessel, and functions to store a substance and release it into the water in a controlled fashion in accordance with this invention.

A "monitor" or "sensor" vessel or vehicle is a vessel that has one or more monitors or sensors for determining a condition of water and/or air at or around the vessel. If the monitor vessel is also a substance distribution vessel, it may process data from the sensors to determine when and how much of the substance is to be deployed at the present location or another location that has been visited. Alternatively, a fleet may contain monitor vessels that are separate from the distribution vessels. In this configuration, information from the monitors is typically transmitted to one or more of the distribution vessels and/or a control center.

The terms "control unit", "central control unit" and "control center" are used interchangeably to refer to an electronic assembly or combination of devices that receives information about one or more conditions of the water at one or more locations, makes decisions about where it is appropriate to distribute fertilizer or another substance from one or more distribution vessels, and sends instructions to the distribution vessels accordingly. The control unit typically runs most of the time without human decision making, but within parameters programmed or provided by and periodically adjusted by human operators. The control unit may be placed anywhere on shore within range to receive and transmit data and instructions to the monitor and substance distribution vessels under its control. It may be aboard an autonomous vessel or manned ship that is separate from the substance distribution and monitoring vessels in the fleet. Alternatively, it may be aboard one of the monitor vessels or substance distribution vessels, optionally integrated with the microcircuitry of that vessel.

A "fertilizer" is a substance comprising an agent that promotes growth of an organism or microorganism. An exemplary fertilizer for use with this invention comprises iron and/or a nitrogen containing organic compound such as urea. It can promote the growth of phytoplankton, and indirectly the growth of fish. Fish food or fish pellets also qualify as a fertilizer insomuch as they promote the growth of fish directly. The fertilizer may be a mixture of one or more active fertilizing agents plus carriers or other excipients that may assist in the storage, granularity, distributability, releasability, bioavailability, and/or stability of the active agents once distributed into the water. Convenient forms of fertilizer for distribution using autonomous vessels are particulates or liquids in which the active agents are dissolved.

For all purposes in the United States of America, each and every publication and patent document cited herein is incorporated herein by reference as if each such publication or document was specifically and individually indicated to be incorporated herein by reference.

While the invention has been described with reference to the specific embodiments, changes can be made and equivalents can be substituted to adapt to a particular context or intended use, thereby achieving benefits of the invention without departing from the scope of what is claimed.

The invention claimed is:

1. A fleet configured for fish stock assessment, the fleet comprising:
    (a) a plurality of autonomous wave-powered monitor vessels, each comprising:
        one or more observational sensor(s) configured for recognizing and monitoring fish in a body of water in which the vessel is situated;
        a positional sensor configured to determine the geographical location of the vessel; and
        a transmitter configured to transmit data wirelessly from the observational and the positional sensors to a central control unit;
    (b) said central control unit, which is configured and programmed to communicate with each of the monitor vessels to direct navigation and to receive and compile data regarding fish being monitored by the monitor vessel; and
    (c) one or more autonomous wave-powered substance distribution vessels, wherein each of the substance distribution vessels is configured to distribute fish food in a body of water in which the substance distribution vessel is situated under command of the central control unit, in accordance with data received from the monitor vessels.

2. The fleet of claim 1, wherein at least some of the monitoring vessels comprise a tow body attached to and pulled behind the vessel, upon which one or more of the observational sensors are deployed.

3. The fleet of claim 1, further comprising one or more stationary units comprising sensor(s) configured for recognizing and monitoring fish,
    wherein each of said stationary units is configured to be deployed at or near the bottom of the body of water, or suspended at a fixed position at a defined depth in the body of water, and
    wherein the one or more vessels in the fleet is a relay vessel that is equipped to receive data regarding fish being monitored by the stationary unit(s) and to convey the data to the central control unit.

4. The fleet of claim 3, wherein the relay vessel(s) comprise a tow body equipped with a modem configured to receive data from the stationary unit(s).

5. The fleet of claim 1, wherein the central control unit is land-based, and the fleet further comprises a satellite that is equipped to relay data from the monitor vessels to the central control unit.

6. The fleet of claim 1, wherein the central control unit is situated on board an autonomous vessel or manned ship.

7. The fleet of claim 1, wherein the monitor vessels each comprise:
    a float that is buoyed to travel on or near the surface of a body of water;
    a swimmer that is weighted to travel in the water below the float, the swimmer comprising fin surfaces that mechanically provide forward thrust when actuated by rising and falling of the swimmer in the water; and
    one or more tethers connecting the float to the swimmer, arranged so that the swimmer pulls the float by way of the tether(s) when the vessel is in wave-bearing water.

8. The fleet of claim 1, wherein the monitor vessels are configured to generate electrical power from wave motion.

9. The fleet of claim 1, wherein at least one of the observational sensors produces image or video data.

10. The fleet of claim 1, wherein at least one of the observational sensors is a fish counting sonar or an acoustic fish tag receiver.

11. The fleet of claim 1, wherein at least one of the vessels in the fleet comprises a tow body configured to contain and release fish food.

12. The fleet of claim 1, wherein at least some of the vessels in the fleet are dual purpose vessels that serve as both monitor vessels and substance distribution vessels.

13. The fleet of claim 1, wherein the central control unit is aboard one of the monitor vessels or substance distribution vessels.

14. A method of assessing fish stock, comprising operating a fleet according to claim 1 such that the monitor vessels recognize and monitor fish in a body of water, and the central control unit receives and compiles data regarding the fish being monitored.

15. A method of fish farming, comprising operating a fleet according to claim 1 such that:
 the monitor vessels recognize and monitor fish in a body of water,
 the central control unit receives and compiles data regarding the fish being monitored and makes decisions as to where it is appropriate to distribute fish food; and
 the substance distribution vessel(s) distribute the fish food in the body of water under command of the central control unit.

16. A fleet configured for fish stock assessment, the fleet comprising:
 (a) a plurality of autonomous wave-powered monitor vessels, each comprising:
  one or more observational sensor(s) configured for recognizing and monitoring fish in a body of water in which the vessel is situated;
  a positional sensor configured to determine the geographical location of the vessel; and
  a transmitter configured to transmit data wirelessly from the observational and the positional sensors to a central control unit; and
 (b) said central control unit, which is configured and programmed to communicate with each of the monitor vessels to direct navigation and to receive and compile data regarding fish being monitored by the monitor vessel;
 wherein the monitor vessels comprise at least one sensor that detects an identifying ingredient of fish food in the form of pellets or powders containing food palatable and nutritious to fish.

17. An autonomous wave powered vessel configured for fish stock assessment, the vessel comprising:
 a float that is buoyed to travel on or near the surface of a body of water;
 a swimmer that is weighted to travel in the water below the float, the swimmer comprising fin surfaces that mechanically provide forward thrust when actuated by rising and falling of the swimmer in the water; and
 one or more tethers connecting the float to the swimmer, arranged so that the swimmer pulls the float by way of the tether(s) when the vessel is in wave-bearing water;
 a positional sensor configured to determine the geographical location of the vessel;
 a tow body configured to be attached to and pulled behind the swimmer, upon which is deployed an observational sensor configured to recognize and monitor or assess fish in a body of water in which the vessel is situated and to monitor or assess the fish, or a modem configured to receive data from such a sensor that is deployed on a stationary unit at or near the bottom of the body of water or suspended at a defined depth; and
 a transmitter configured to wirelessly transmit to a central control unit data from the observational sensor regarding fish being monitored by the vessel, and data from the positional sensor regarding the geographical location of the vessel;
 wherein the tow body is configured to contain and release fish food.

18. A fleet configured for fish stock assessment, the fleet comprising:
 (a) a plurality of autonomous wave-powered monitor vessels, each comprising:
  one or more observational sensor(s) configured for recognizing and monitoring fish in a body of water in which the vessel is situated;
  a positional sensor configured to determine the geographical location of the vessel; and
  a transmitter configured to transmit data wirelessly from the observational and the positional sensors to a central control unit; and
 (b) said central control unit, which is configured and programmed to communicate with each of the monitor vessels to direct navigation and to receive and compile data regarding fish being monitored by the monitor vessel;
 wherein the central control unit is programmed to compile data from the monitor vessels, and to determine therefrom how much fish food is to be dispensed and where vessels distributing fish food should travel.

19. The fleet of claim 18, wherein the data includes data obtained from counting equipment aboard the monitor vessels for fish of a desired size.

* * * * *